US012558399B2

(12) United States Patent
Macchi

(10) Patent No.: US 12,558,399 B2
(45) Date of Patent: Feb. 24, 2026

(54) ISOCYCLOSPORIN A FOR TOPICAL TREATMENT OF OCULAR DISEASES

(71) Applicant: DOMPE' FARMACEUTICI S.P.A., Milan (IT)

(72) Inventor: Ilaria Macchi, Rome (IT)

(73) Assignee: Dompe' Farmaceutici S.P.A., Milan (IT)

( * ) Notice: Subject to any disclaimer, the term of this patent is extended or adjusted under 35 U.S.C. 154(b) by 0 days.

(21) Appl. No.: 18/722,415

(22) PCT Filed: Dec. 22, 2022

(86) PCT No.: PCT/EP2022/087581
§ 371 (c)(1),
(2) Date: Jun. 20, 2024

(87) PCT Pub. No.: WO2023/118487
PCT Pub. Date: Jun. 29, 2023

(65) Prior Publication Data
US 2025/0082719 A1     Mar. 13, 2025

(30) Foreign Application Priority Data
Dec. 24, 2021    (EP) .................................... 21217735

(51) Int. Cl.
| | |
|---|---|
| *A61K 38/13* | (2006.01) |
| *A61K 9/00* | (2006.01) |
| *A61K 45/06* | (2006.01) |
| *A61P 29/00* | (2006.01) |

(52) U.S. Cl.
CPC ............ *A61K 38/13* (2013.01); *A61K 9/0048* (2013.01); *A61K 45/06* (2013.01); *A61P 29/00* (2018.01)

(58) Field of Classification Search
None
See application file for complete search history.

(56) References Cited

U.S. PATENT DOCUMENTS

| | | | |
|---|---|---|---|
| 6,867,400 | B2 | 3/2005 | Collins et al. |
| 2019/0194258 | A1 | 6/2019 | Li et al. |

FOREIGN PATENT DOCUMENTS

| | | | | |
|---|---|---|---|---|
| GB | 2224205 A | 5/1990 | | |
| WO | WO 1993/017039 A1 | 9/1993 | | |
| WO | WO-9317039 A1 * | 9/1993 | ............. | C07K 7/645 |
| WO | WO 2023/118487 A1 | 6/2023 | | |
| WO | WO 2023/119173 A1 | 6/2023 | | |

OTHER PUBLICATIONS

Chennell et al. "Stability of an ophthalmic micellar formulation of cyclosporine A in unopened multidose eyedroppers and in simulated use conditions" Eur. J. Pharm. Sci. 100:230-237. (Year: 2017).*

Ismail et al. "Topical cyclosporin as an alternative treatment for vision threatening blepharokeratoconjunctivitis: a case report" Intl. Med. Case Rep. J. 2012:33-37 (Year: 2012).*
De Paiva et al. "Topical cyclosporine A therapy for dry eye syndrome (Review)" Cochrane Database of Systematic Reviews 2019: CD010051. (Year: 2019).*
Arkin et al., "FLIPR™ Assays for GPCR and Ion Channel Targets", Assay Guidance Manual, Eli Lilly & Company and the National Center for Advancing Translational Sciences Bethesda (MD), 2004, updated Oct. 2012, pp. 581-584.
Bundgaard et al., "Prodrugs of peptides. 16. Isocyclosporin A as a potential prodrug of cyclosporin A", International Journal of Pharmaceutics, Apr. 1992, 82(1-2):85-90.
Carpino et al., "Dramatically enhanced N-O acyl migration during the trifluoroacetic acid-based deprotection step in solid phase peptide synthesis", Tetrahedron Letters, Feb. 2005, 46(8):1361-1364.
Cuajungco et al., "The Mucolipin-2 (TRPML2) Ion Channel: a tissue-specific protein crucial to normal cell function," Pflugers Arch., Feb. 2016, 468(2):177-192.
De La Hoz et al., "Microwaves in organic synthesis. Thermal and non-thermal microwave effects," Chemical Society Reviews, Jan. 2005, 34(2):164-178.
De Oliveira et al., "Practical guidance for the use of cyclosporine ophthalmic solutions in the management of dry eye disease," Clinical Ophthalmology, Jul. 2019, 13:1115-1122.
Draize et al., "Methods for the Study of Irritation and Toxicity of Substances Applied Topically to the Skin and Mucous Membranes," Journal of Pharmacology and Experimental Therapeutics, Nov. 1944, 82(3):377-390.
Feroze et al., "Ciclosporin A in ophthalmology: A systematic review," Kerala Journal of Ophthalmology, Sep.-Dec. 2019. 31(3):182-190.
Friis et al., "Kinetics of degradation of cyclosporin A in acidic aqueous solution and its implication in its oral absorption," International Journal of Pharmaceutics, Apr. 1992, 82(1-2): 79-83.
International Preliminary Report on Patentability in International Appln. No. PCT/EP2022087581, mailed on July 4, 202024, 13 pages.
International Search Report and Written Opinion in International Appln. No. PCT/EP2022087581, mailed on Apr. 12, 2023, 17 pages.
International Search Report and Written Opinion in International Appln. No. PCT/IB2022/0625576, mailed on Apr. 12, 2023, 10 pages.
International Search Report and Written Opinion in International Appln. No. PCT/IB2022/062583, mailed on Apr. 12, 2023, 7 pages.
Jerkins et al., "A Review of Topical Cyclosporine A Formulations—A Disease-Modifying Agent for Keratoconjunctivitis Sicca," Clinical Ophthalmology, Feb. 2020, 14:481-489.
Lallemand et al., "Cyclosporine A delivery to the eye: A pharmaceutical challenge," European Journal of Pharmaceutics and Biopharmaceutics, Nov. 2003, 56(3):307-318.
Li et al., "A controlled-release ocular delivery system for ibuprofen based on nanostructured lipid carriers," International Journal of Pharmaceutics, Nov. 2008, 363(1-2):177-182.

(Continued)

*Primary Examiner* — Melissa L Fisher
*Assistant Examiner* — Zachary J Miknis
(74) *Attorney, Agent, or Firm* — Fish & Richardson P.C.

(57) ABSTRACT

The present invention relates to isocyclosporin A, salts and ophthalmic compositions thereof for ophthalmic topical use in the prevention or treatment in an individual of an ophthalmic inflammatory and/or autoimmune disease, preferably selected from corneal and ocular surface inflammatory and/or autoimmune diseases and eyelid margin inflammatory diseases.

20 Claims, 2 Drawing Sheets

(56)                   References Cited

OTHER PUBLICATIONS

Makino et al., "Development of an efficient semisynthetic modification of FR901459 via a novel regioselective N, O-acyl migration," Bioorganic & Medicinal Chemistry Letters, May 2020, 30(14), 127251.

Oliyai et al., "Kinetics and mechanism of isomerization of cyclosporin A," Pharmaceutical Research, May 1992, pp. 617-622.

Plesch et al., "Selective agonist of TRPML2 reveals direct role in chemokine release from innate immune cells," eLife Sciences, Nov. 2018, 7:e39720, 23 pages.

Prabhu et al., "Topical cyclosporine A 0.05% for recurrent anterior uveitis, " British Journal of Ophthalmology, Mar. 2016, 100(3):345-347.

Rossi et al., "Bevacizumab eye drop treatment stimulates tear secretion in rats through changes in VEGF and NGF lacrimal gland levels," Arch Ital Biol., Mar. 2012, 150(1):15-21.

Schwochert et al., "Revisiting N-to-O Acyl Shift for Synthesis of Natural Product-like Cyclic Depsipeptides," Organic Letter Dec. 2014, 16(23):6088-916088.

Survase et al., "Cyclosporin A—A review on fermentative production, downstream processing and pharmacological applications," Biotechnology Advances, Jul. 2011, 29(4):418-435.

Thalluri et al., "Microwave assisted chemoselective organocatalytic peptide alcohol synthesis from C-terminal amide," RSC Advances, Sep. 2014, 4(88):617-623.

Yamada et al., "Functional expression of transient receptor potential vanilloid 3 (TRPV3) in corneal epithelial cells: Involvement in thermosensation and wound healing," Experimental Eye Research, Jan. 2010, 90(1):121-129.

Yang et al., "TRPC4 Knockdown Suppresses Epidermal Growth Factor-induced Store-operated Channel Activation and Growth in Human Corneal Epithelial Cells*" Oct. 2010, The Journal of Biological Chemistry, 280(37):32230-32237.

Yeh et al., "Apoptosis of ocular surface cells in experimentally induced dry eye," Invest. Ophthalmol. Vis. Sci., Jan. 2003, 44(1):124-129.

Applicant Response in European Appln. No. 22844376.6, filed on Nov. 28, 2023, 51 pages.

Office Action in European Appln. No. 22844376.6, mailed on Sep. 25, 2024, 53 pages.

Applicant Response in European Appln. No. 22844376.6, filed on Nov. 14, 2024, 45 pages.

Office Action in European Appln. No. 22844376.6, mailed on Jan. 9, 2025, 60 pages.

Applicant Response in European Appln. No. 22844376.6, filed on Jan. 15, 2025, 42 pages.

Office Action in European Appln. No. 22844376.6, mailed on Jan. 29, 2025, 53 pages.

* cited by examiner

ISOCYCLOSPORIN A FOR TOPICAL TREATMENT OF OCULAR DISEASES

CROSS REFERENCE TO RELATED APPLICATION

This application is a U.S.C. § 371 National Stage application from PCT/EP2022/087581 filed Dec. 22, 2022, which claims the benefit of European Application No. 21217735.6 filed Dec. 24, 2021, the disclosures of which are incorporated herein by reference.

FIELD OF THE INVENTION

The present invention relates to isocyclosporin A, salts and pharmaceutical compositions thereof and to their use in the prevention or treatment in an individual of an inflammatory and/or autoimmune ophthalmic disease.

STATE OF THE ART

Cyclosporin A is a neutral, lipophilic, cyclic undecapeptide obtained from the fungus *Tolypocladium Inflatum*, containing seven N-methyl aminoacid residues and the unusual aminoacid (4R)-4-([E]-2-butenyl)-4-N-methyl-(L)-threonine (MeBmt) at position 1.

Cyclosporin was first approved for use as an immunosuppressive agent for the prevention of organ rejection of transplanted organs.

In ophthalmology, cyclosporin A was initially investigated for administration after corneal graft transplantation but later showed to be effective also in a number of inflammatory diseases of the eye, such as uveitis, vernal keratoconjunctivitis (VKC), keratoconjunctivitis (AKC) and dry eye disease (DED) (Feroze et al, J Ophthalmol 2019, 31:182-190; Prabhu et al, British Journal of Ophthalmology 2016, 100:345-347).

Due to its hydrophobicity, the molecule was initially administered also for ophthalmic indications via systemic routes such as by intravenous injection or oral administration. These routes of administration allowed to reach therapeutic concentration of the active in intraocular fluids (aqueous or vitreous humor) and extraocular organs or annexes (cornea, conjunctiva and lachrymal glands). However, the occurrence of serious systemic side effects, such as nephrotoxicity and hypertension, prompted the study of formulations suitable for topical administration of the molecule (Lallemand et al, European Journal of Pharmaceutics and Biopharmaceutics 2003, 56:307-318).

The development of eye drops formulations of cyclosporin A for ophthalmic topical use has been hindered by the hydrophobicity and extremely low aqueous solubility (6.6 mg/ml) of the molecule, that do not allow the preparation of formulations based on the commonly used aqueous ophthalmic vehicles.

Cyclosporin A was initially formulated in form of solutions in oil-based solvents such as castor oil or corn oil, but these were later replaced by oil-in-water emulsions and micelle based solutions (de Oliveira et al, Clinical Ophthalmology 2019:13 1115-1122).

However, it has been found that the necessary presence of surfactant in the latter formulations has a deleterious effects on the cornea and results in blurred vision. Furthermore, although emulsions have the advantage of rapid ocular spreading upon application, low bioavailability of lipophilic drugs from emulsions still limits the amount of active principle available in an already challenging aqueous ocular environment (Jerkins et al, Clinical Ophthalmology 2020:14 481-489).

The poor solubility of cyclosporin and the presence in most of the ophthalmic formulations currently available of surfactants having deleterious effects on the cornea, are key limitations for the use of cyclosporin in the context of ophthalmological treatments, possibly also accounting for the poor tolerability and the high variability in response reported in clinical trials.

Isocyclosporin A is an isomer of cyclosporin A that differs from the latter in that residue (N-methyl-(4R)-4-but-2E-en-1-yl-4-methyl-(L) threonyl) at position 1 is linked to the residue at position 11 via 3'-O-atom rather than the N-atom. Isocyclosporin A has originally been identified as a rearranged degradation product formed by acid treatment of cyclosporin A. Isocyclosporin A has been described as devoid of any biological activity per se and, when administered systemically, very slowly converting in vivo to the corresponding active cyclosporin form (WO1993017039A1, page 5 and page 15). In particular, the molecule has been shown to undergo a quantitative conversion to cyclosporin A at a pH higher than 5. In detail, the rate of isomerization of isocyclosporin is maximum at pH between 8 and 10 (Oliyai R, Stella V J, Pharm Res, 1992 May; 9 (5): 617-22), while the slowest rate of conversion is observed at the pH range between 6 and 8. In particular, at pH 7.4 the conversion is minimal, with a half-life of the conversion of 21.7 hours (see Bundgaard et al, International Journal of Pharmaceutics, 82 (1992): 85-90).

In view of the ability to slowly convert to cyclosporin A and of the higher solubility in water, isocyclosporin A has been suggested for use as a prodrug of cyclosporin A for oral administration, in order to improve stability and avoid side effects associated to peak blood concentrations of cyclosporin.

In this respect, WO 1993017039A1 describes acid addition salts of isocyclosporins, including isocyclosporin A, that provide improved galenic characteristics, such as enhanced solubility and stability. The document discloses that these salts are particularly useful as pro-drugs for oral administration of cyclosporin, since, when administered orally, they release the active molecule at a slow rate, maintaining constant levels of cyclosporin in the blood.

However, the local ophthalmic use of isocyclosporin A has been considered not practicable in view of the slow conversion rate of the molecule in that environment. In fact, the rate of interconversion of isocyclosporin A to cyclosporin A is so low that during the residence time of the molecule on the ocular surface, substantially no cyclosporin A is formed. As discussed above, it has been described that at pH values between 6 and 8 there is the slowest conversion and, in particular, at pH 7.4 the time for 50% of conversion from isocyclosporin A to cyclosporin A is 21.7 hours (Bundgaard et al, International Journal of Pharmaceutics, 82 (1992): 85-90).

In view of the above, in the Applicant knowledge, isocyclosporin A was never considered a feasible alternative to the cyclosporin A for local ophthalmic applications since it was not expected to exert any pharmacological activity.

SUMMARY OF THE INVENTION

The Applicant has now surprisingly found that isocyclosporin A, when administered topically to the eye, unexpectedly shows a biological activity that is independent from its conversion to cyclosporin A. As discussed above, this finding is completely unpredictable based on the background literature.

Even more surprisingly, as shown in the experimental section by in vivo tests conducted on a relevant animal model of inflammatory ocular surface disease, the Applicant observed that isocyclosporin A treatment shows a higher efficacy on several pharmacologically relevant parameters compared to cyclosporin A.

The present inventors have also found that isocyclosporin A is able to inhibit the activity of TRPV3 and TRPML2 ionic channels that have been described in the literature as being involved in the symptomatology of inflammatory and allergic diseases (Takahiro Yamada et al, Exp Eye Res. 2010 January; 90 (1): 121-129; MP Cuajungco et al, Pflugers Arch. 2016 February; 468 (2): 177-92; and Eva Plesch et al, eLife. 2018; 7: e39720). Furthermore, contrary to cyclosporin A, isocyclosporin A does not stimulate epithelial cells hyperproliferation induced by activation of the TRPC4 channel, which is undesired in inflammatory and allergic ocular diseases.

Accordingly, a first object of the invention is isocyclosporin A or an ophthalmically acceptable salt thereof for ophthalmic topical use in the prevention or treatment of an inflammatory and/or autoimmune ophthalmic disease.

Preferably, said inflammatory and/or autoimmune ophthalmic disease is selected from corneal and ocular surface inflammatory and/or autoimmune diseases and eyelid margin inflammatory diseases.

A second object of the invention is an ophthalmic formulation comprising isocyclosporin A or an ophthalmically acceptable salt thereof and at al least one ophthalmically acceptable excipient or diluent.

A further object of the invention is a method for the prevention or treatment of an inflammatory and/or autoimmune ophthalmic disease, preferably selected from corneal and ocular surface inflammatory and/or autoimmune diseases and eyelid margin inflammatory diseases, which comprises topically administering to an individual in need thereof an effective amount of isocyclosporin A or of an ophthalmically acceptable salt thereof and/or of an ophthalmic formulation thereof.

DETAILED DESCRIPTION OF THE INVENTION

Figure 1:
FIG. 1 shows the percentage of fluorescence reported as a mean of the values measured for each group at day 0, 9, 11, 17, 22 and 25 after scopolamine treatment, as described in Example 1.

A first object of the invention is isocyclosporin A or an ophthalmically acceptable salt thereof for ophthalmic topical use in the prevention or treatment in an individual of an inflammatory and/or autoimmune ophthalmic disease.

Preferably, said inflammatory and/or autoimmune disease is selected from corneal and ocular surface inflammatory and/or autoimmune diseases and eyelid margin inflammatory diseases.

Corneal and ocular surface inflammatory and/or autoimmune diseases are diseases characterized by damage of the epithelium that covers the cornea and the conjunctiva induced by the local inflammatory status Eyelid margin inflammatory diseases are diseases characterized by common and persistent inflammation of the eyelids.

In particular, according to the invention, said ophthalmic inflammatory and/or autoimmune disease is selected from vernal keratoconjunctivitis (VKC), atopic keratoconjunctivitis (AKC), allergic conjunctivitis, ocular rosacea, uveitis, dry eye disease (DED), ocular cicatricial pemphigoid (OCP), ocular graft-versus-host disease (GVHD), immune corneal ulcers, inflamed pterygium and chronic blepharitis.

According to the present invention, said isocyclosporin A or salt thereof is administered topically to the eye of said individual.

According to the present invention, the term "prevention" refers to partial or complete prevention of a disorder or pathological event, before this is established or occurs.

According to one embodiment of the invention, prevention is a complete prevention, wherein the disorder or pathological event is completely blocked.

According to an alternative embodiment of the invention, prevention is a partial prevention, wherein the development of the disorder or pathological event is delayed and/or its severity is reduced.

According to the present invention, the term "treatment" refers to complete reversal or to the reduction of severity or progression of a disorder or pathological event, after this is already established or occurred.

According to the present invention, the term "individual" refers to a human or an animal being, preferably to a human being.

Preferably, said inflammatory and/or autoimmune ophthalmic disease that can be treated using the isocyclosporin A or an ophthalmically acceptable salt thereof is an ophthalmic disease that shows improvement or recovery upon treatment with cortisone and similar corticosteroids.

Corneal and ocular surface inflammatory and/or autoimmune diseases that can be treated using isocyclosporin A or an ophthalmically acceptable salt thereof are preferably selected from vernal keratoconjunctivitis (VKC), atopic keratoconjunctivitis (AKC), allergic conjunctivitis, ocular rosacea, uveitis, dry eye disease (DED), ocular cicatricial pemphigoid (OCP), ocular graft-versus-host disease (GVHD) and immune corneal ulcers. Preferably, said allergic conjunctivitis is a seasonal or perennial allergic conjunctivitis.

Eyelid margin inflammatory diseases that can be treated using isocyclosporin A or an ophthalmically acceptable salt thereof are for instance inflamed pterygium and chronic blepharitis.

According to the invention, preferably said isocyclosporin A or an ophthalmically acceptable salt thereof can be used for the prevention and the treatment of one, two or more inflammatory and/or autoimmune ophthalmic diseases above indicated.

According to the present invention, said isocyclosporin A or said salt thereof is applied topically on the ocular surface of the eye of said individual or on the eyelid margin.

According to a preferred embodiment, said isocyclosporin A or said salt thereof is applied topically on the ocular surface of the eye of said individual by means of an ophthalmic liquid or semiliquid formulation, as will be described below.

Preferably, said isocyclosporin A or said salt thereof is administered once, twice, three times, four times, or more, daily, depending on the medical circumstances and the severity of the disease to be treated.

According to a preferred embodiment of the invention, said ophthalmically acceptable salt is an acid addition salt of isocyclosporin A.

Preferably, said ophthalmically acceptable salt of isocyclosporin A is selected from acetate, adipate, ascorbate, benzoate, benzenesulfonate, bicarbonate, bisulfate, butyrate, camphorate, camphorsulfonate, citrate, cyclohexyl sulfamate, ethanesulfonate, fumarate, glutamate, glycolate, hemisulfate, 2-hydroxyethylsulfonate, heptanoate, hexanoate, hydrochloride, hydrobromide, hydroiodide, hydroxymaleate, lactate, malate, maleate, methanesulfonate, 2-naphthalenesulfonate, nitrate, oxalate, pamoate, persulfate, phenylacetate, phosphate, diphosphate, picrate, pivalate, propionate, quinate, salicylate, stearate, succinate, sulfamate, sulfanilate, sulfate, tartrate, tosylate (p-toluenesulfonate), trifluoroacetate and undecanoate salts of isocyclosporin A.

More preferably, said salt is a hydrochloride or a trifluoroacetate salt of isocyclosporin A.

The acid addition salts of the invention are preferably formed at the alpha-N atom of the residue at the position 1 of the isocyclosporin A.

Methods of preparation of the salts according to the invention are well known and described, for example, in patent application WO1993017039A1.

A second object of the invention is an ophthalmic formulation comprising isocyclosporin A or an ophthalmically acceptable salt thereof, as defined above, as active ingredient and at least one ophthalmically acceptable excipient or diluent.

According to a preferred embodiment, said ophthalmic formulation is a liquid ophthalmic formulation, preferably an eye drop liquid formulation.

The above liquid ophthalmic formulation may be a monophasic liquid formulation, preferably a solution, more preferably an aqueous solution or a biphasic liquid formulation, preferably an emulsion, more preferably a micro-emulsion.

The above liquid ophthalmic formulation preferably contains a physiological saline solution as vehicle.

According to another preferred embodiment, said ophthalmic formulation is a semi-solid ophthalmic formulation, preferably a cream, ointment or gel.

According to yet another preferred embodiment, said ophthalmic formulation is a solid ophthalmic formulation for the extemporaneous preparation of a liquid or semi-solid ophthalmic formulation, as described above, by addition of an ophthalmologically acceptable diluent before administration.

Preferably, said solid ophthalmic formulation is in form of a powder, more preferably it is in the form of a lyophilized powder.

Preferably, said liquid or semi-solid ophthalmic formulation has a pH comprised between 6 and 8, more preferably between 6.4 and 7.8, even more preferably between 6.5 and 7.5. In fact, it is known that at these conditions, the rate of interconversion of isocyclosporin A to cyclosporin A is minimal, thus assuring the stability of the final product (at pH 7.4, 37° C., 50% conversion takes 21.7 hours Bundgaard et al, International Journal of Pharmaceutics, 82 (1992): 85-90).

Preferably, said liquid or semi-solid ophthalmic formulation contains a buffer able to maintain the formulation at the desired pH.

The buffer is preferably selected from, but is not limited to, acetate buffers, carbonate buffers, citrate buffers, phosphate buffers and borate buffers. Acids or bases may be used to adjust the pH of these formulations as needed.

Preferably, the ophthalmic formulation according to the invention also contains one or more excipients selected from ophthalmically acceptable surfactants, preservatives, stabilizers, tonicity adjustors, viscosity modifiers, antioxidants and chelating agents.

The surfactant(s) may be used for assisting in dissolving an excipient or the active agent, dispersing a solid or liquid in a composition, enhancing wetting, modifying drop size, or a number of other purposes.

Preferably, surfactants contained in the ophthalmic formulation according to the invention are selected from alcohols, amine oxides, block polymers, carboxylated alcohol or alkylphenol ethoxylates, carboxylic acids/fatty acids, ethoxylated alcohols, ethoxylated alkylphenols, ethoxylated aryl phenols, ethoxylated fatty acids, ethoxylated fatty esters or oils (animal and vegetal), fatty esters, fatty acid methyl ester ethoxylates, glycerol esters, glycol esters, lanolinbased derivatives, lecithin and lecithin derivatives, lignin and lignin derivatives, methyl esters, monoglycerides and derivatives, polymeric surfactants, propoxylated and ethoxylated fatty acids, alkyl phenols, protein-based surfactants, sarcosine derivatives, sorbitan derivatives, sucrose and glucose esters and derivatives.

Preferably, preservatives contained in the ophthalmic formulation according to the invention are selected from cationic preservatives, preferably quaternary ammonium compounds, more preferably benzalkonium chloride or polyquad; guanidine-based preservatives, preferably PHMB or chlorhexidine; chlorobutanol; mercury preservatives, preferably selected from thimerosal, phenylmercuric acetate and phenylmercuric nitrate; oxidizing preservatives, preferably stabilized oxychloro complexes, more preferably stabilized chlorine dioxides, such as, for example the commercial product Purite®; parabens, such as methylparaben and polypropylparaben.

According to one embodiment, the ophthalmic formulation according to the invention does not contain preservatives.

Preferably, tonicity adjustors contained in the ophthalmic formulation according to the invention are selected from salts, preferably sodium chloride, potassium chloride, magnesium chloride, calcium chloride, sorbitol, trehalose, mannitol and glycerine.

Preferably, the viscosity at room temperature of the ophthalmic formulation according to the invention is between 25 and 50 cps. Viscosity modifiers may be added to the formulation to reach the desired viscosity.

Preferably, viscosity modifiers contained in the ophthalmic liquid formulation according to the invention are selected from polyvinyl alcohol, poloxamers, hyaluronic acid, carbomers, acrylates, cellulose derivatives, dextrans, polyacrylic acids, povidone, polyethylene glycols, propylene glycol, chitosans, gellan gum, and xanthan gum. Preferably, said cellulose derivatives are selected from hydroxypropyl methyl cellulose, carboxymethyl cellulose and hydroxyethyl cellulose.

Preferably, antioxidants contained in the ophthalmic formulation according to the invention are selected from citrate, L-methionine, cysteine, sodium metabisulfite, sodium thiosulfate, acetylcysteine, butylated hydroxyanisole and butylated hydroxytoluene.

Preferably the chelating agent contained in the ophthalmic formulation according to the invention is edetate disodium.

Preferably, when said liquid ophthalmic formulation is an emulsion, it further contains one or more oils.

Preferably said oils are selected from anise oil, castor oil, clove oil, cassia oil, cinnamon oil, almond oil, corn oil, arachis oil, cottonseed oil, safflower oil, maize oil, linseed oil, rapeseed oil, soybean oil, olive oil, caraway oil, rosemary oil, peanut oil, peppermint oil, sunflower oil, eucalyptus oil and sesame oil.

According to a preferred embodiment, the formulation according to the invention does not contain ethanol.

The ophthalmic formulation according to the invention can further comprise one or more drugs used for the prevention or treatment of inflammatory and/or autoimmune ophthalmic diseases and/or a cyclosporin.

A further object of the invention is the above formulation for ophthalmic topical use in the prevention or treatment in an individual of an inflammatory and/or autoimmune ophthalmic disease selected from corneal and ocular surface inflammatory and/or autoimmune diseases and eyelid margin inflammatory diseases, as above defined. The present description also relates to a method for the prevention or treatment of at least one inflammatory and/or autoimmune ophthalmic disease selected from corneal and ocular surface inflammatory and/or autoimmune diseases and eyelid margin inflammatory diseases which comprises topically administering to an individual in need thereof an effective amount of isocyclosporin A or of an ophthalmically acceptable salt thereof and/or of an ophthalmic formulation as above described.

Corneal and ocular surface inflammatory and/or autoimmune diseases that can be treated using isocyclosporin A or an ophthalmically acceptable salt thereof are preferably selected vernal from keratoconjunctivitis (VKC), atopic keratoconjunctivitis (AKC), allergic conjunctivitis, ocular rosacea, uveitis, dry eye disease (DED), ocular cicatricial pemphigoid (OCP), ocular graft-versus-host disease (GVHD) and, immune corneal ulcers.

Preferably, said allergic conjunctivitis is a seasonal or perennial allergic conjunctivitis.

Eyelid margin inflammatory diseases that can be treated using isocyclosporin A or an ophthalmically acceptable salt thereof are inflamed pterygium and chronic blepharitis.

According to the invention, the method of treatment includes the ophthalmic topical administration of isocyclosporin A or an ophthalmically acceptable salt thereof and/or of an ophthalmic formulation as above described for the prevention and the treatment of one, two or more inflammatory and/or autoimmune ophthalmic diseases above indicated.

Preferably, said isocyclosporin A or said salt thereof, or the ophthalmic formulation is applied topically on the ocular surface of the eye of said individual or on the eyelid margin According to a preferred embodiment, said isocyclosporin A or said salt thereof is applied topically on the ocular surface of the eye of said individual by means of an ophthalmic liquid or semiliquid formulation.

Preferably, said isocyclosporin A or said salt thereof is administered once, twice, three times, four times, or more, daily, depending on the medical circumstances and the severity of the disease to treated.

According to an embodiment, the method of treatment includes the ophthalmic topical administration of isocyclosporin A or an ophthalmically acceptable salt thereof and/or of an ophthalmic formulation as above described together with the administration of one or more drugs used for the prevention or treatment of inflammatory and/or autoimmune ophthalmic diseases.

Drugs commonly used for the treatment of inflammatory and/or autoimmune ophthalmic diseases corticosteroids and other anti-inflammatory, immunosuppressive and/or immunomodulatory drugs known in the art.

In one embodiment, the method of treatment includes the administration of isocyclosporin A or an ophthalmically acceptable salt thereof and/or of an ophthalmic formulation as above described together with the administration of a cyclosporin.

The ophthalmic topical administration of isocyclosporin A or an ophthalmically acceptable salt thereof or an ophthalmic formulation can be before, at the same time or after the administration of the one or more drugs commonly used for the treatment of inflammatory and/or autoimmune ophthalmic diseases.

According to a particularly preferred embodiment, said inflammatory and/or autoimmune ophthalmic disease that can be treated using isocyclosporin A or an ophthalmically acceptable salt thereof and/or an ophthalmic formulation thereof is an ophthalmic disease that shows improvement or recovery upon treatment with cortisone and similar corticosteroids.

Therefore, according to this preferred embodiment, the isocyclosporin A or an ophthalmically acceptable salt thereof or an ophthalmic formulation comprising isocyclosporin A and at least one ophthalmically acceptable excipient or diluent, are administered before, at the same time or after the treatment with cortisone and similar corticosteroids.

EXPERIMENTAL SECTION

Example 1—Corneal Fluorescein Staining

The efficacy of an isocyclosporin A eye drop formulation was assessed in a mouse model of scopolamine-induced corneal epithelial damage.

In details, 15 mice (N=5 per group) were randomly assigned at baseline to 3 groups and dry eye was induced by treatment with a subcutaneous injection protocol of 0.5 mg/0.2 ml scopolamine hydrobromide, as previously described (Yeh S et al. Invest Ophthalmol Vis Sci, 2003, 44 (1): 124-9).

Experimental groups consisted in a control group, that did not receive any eye drop treatment ("CTRL" group) and two treatment groups, one treated with a traditional cyclosporin A trifluoroacetate ophthalmic suspension, containing 0.05% cyclosporin A trifluoroacetate in phosphate buffer with 2% Tween 80 ("Old" group) and the other treated with a corresponding isocyclosporin A trifluoroacetate ophthalmic solution ("New" group) containing 0.05% isocyclosporin A trifluoroacetate in phosphate buffer with 2% Tween 80.

In the treatment groups, ten microliters of the test formulations were instilled in each mouse three times a day in both eyes starting at Day 1 after the first scopolamine injection for 25 days. The treatments were encoded, and the group allocation was blinded to the technician administering the treatment, and to the researcher assessing the outcome of the experiment. Group identification was uncovered at the end of the analysis.

In vivo fluorescein staining was performed in each group at day 0, 9, 11, 17, 22 and 25 after scopolamine treatment in order to determine any corneal epithelial defects. Corneal fluorescein staining is a valuable clinical tool to assess the viability of the epithelium.

Digital images were obtained under slit lamp with a cobalt blue light at 10× magnification analysed in a semi-automatic manner for fluorescein staining using ImageJ software.

As shown FIG. 1, a lower epithelial damage (as shown by corneal fluorescein staining) was observed in the group treated with isocyclosporin A ophthalmic solution (New) compared to the groups treated with cyclosporin A (Old) or with no treatment.

Of interest, this effect was greater in the first 17 days of the study, reaching statistical significance at day 9, which suggests a direct effect of the isocyclosporin formulation on corneal epithelial healing that is unrelated to the prolonged lubrication.

Tear secretion was also measured in all animals by modified Schirmer test at day 22 and at day 25, as described in Rossi S. et al. Arch Ital Biol. 2012 March; 150 (1): 15-21.

Figure 2:
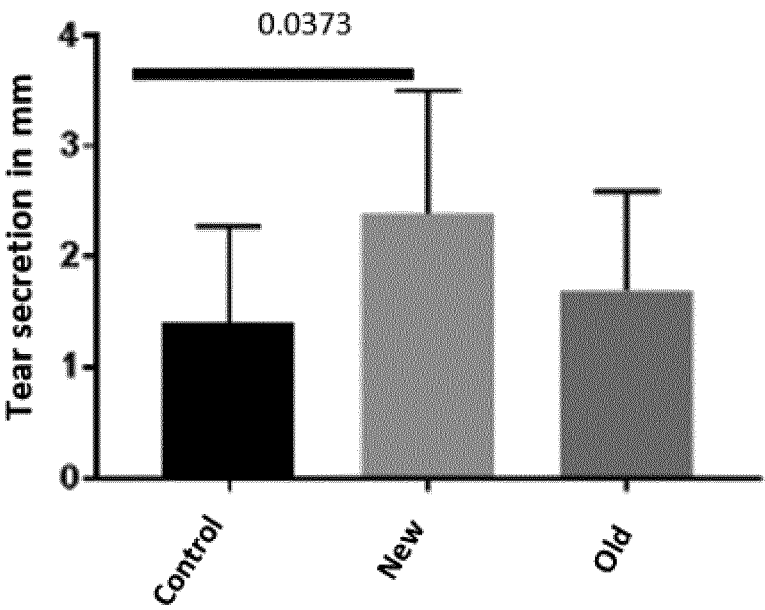
FIG. 2 shows the mm of tear secretion measured in the three experimental groups at 22 days (upper panel) and 25 days (lower panel) after scopolamine treatment, as described in Example 1.
Figure 2:
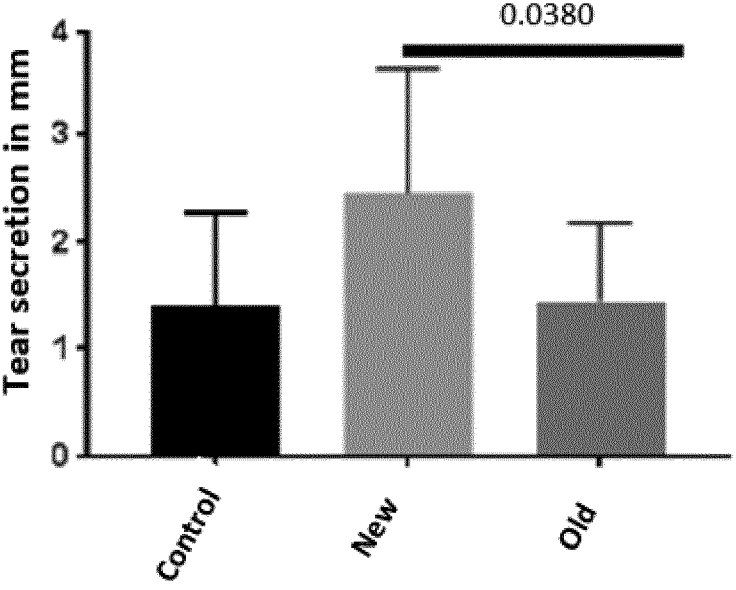

As can be seen in FIG. 2, a significant difference was also observed between the different treated groups in tear secretion at both timepoints, with significantly higher levels in the isocyclosporin-treated group.

In sample animals, the levels of absorbed cyclosporin and isocyclosporin in ocular tissues were also assessed. Biopsies of relevant tissues were taken at three different timepoints, i.e. day 1 (5 min after first treatment), day 2 (5 min after first treatment) and day 7 (5 min after first treatment) in a subgroup of 3 mice/group.

Tissues were centrifuged, homogenized, lyophilized. 1 mg of lyophilized tissue was extracted with EtOAc (0.5 ml) at room temperature and the organic solution was analysed by HPLC to assess tissue concentration and relative amount of cyclosporin A and Isocyclosporin A.

The chromatographic conditions of HPLC analysis are reported in Table A and Table B below:

TABLE A

| HPLC | HPLC Alliance with PDA detector |
|---|---|
| Column | X Bridge C18, 5 μm 150 * 4.6 mm |
| Injection volume | 10 UL |
| Detector | 210 nm |
| Flow rate | 1.50 ml/min |
| Run time | 26 minutes |
| Column Temperature | 65° C. ± 5° C. |
| Sample Temperature | 24° C. ± 5° C. |
| Conc. for purity | 0.5 mg/ml in acetonitrile |
| Conc. for assay | 0.2 mg/ml in acetonitrile |
| Sample preparation | Without any treatment (injected as is) |

TABLE B

Mobile phase (Gradient)

| | Time (min) | Flow Rate (ml/min) | TFA 0.05% in H$_2$O (A) | TFA 0.05% in CH$_3$CN (B) |
|---|---|---|---|---|
| 1 | 0.00 | 1.50 | 60.0 | 40.0 |
| 2 | 0.50 | 1.50 | 60.0 | 40.0 |
| 3 | 15.00 | 1.50 | 20.0 | 80.0 |
| 4 | 19.00 | 1.50 | 20.0 | 80.0 |
| 5 | 20.00 | 1.50 | 60.0 | 40.0 |
| 6 | 25.00 | 1.50 | 60.0 | 40.0 |

Mobil Phase A:
0.5 ml of trifluoroacetic acid (TFA) dissolved in 1000 ml of water.
Mobil Phase B:
0.5 ml of trifluoroacetic acid (TFA) dissolved in 1000 ml of acetonitrile.
The data obtained show a higher biodistribution in ocular surface and intraocular tissues for isocyclosporin A compared to cyclosporin A (>10 fold) and significantly lower variability within different animals with the same treatment.

The mean levels (ng/mg) detected for isocyclosporin A and cyclosporin A in cornea, conjunctiva and intraocular tissues (sclera and uvea) are reported in Table C below:

TABLE C biodistribution of isocyclosporin A and cyclosporin A in cornea, conjunctiva and intraocular tissues

| | Cornea | Conjunctiva | Intraocular tissues (combined) |
|---|---|---|---|
| Isocyclosporin A | 15 ± 5 ng/mg | 20 ± 7 ng/mg | 2 ± 1 ng/mg |
| Cyclosporin A | 1 ± 1 ng/mg | 2 ± 1 ng/mg | Not detectable |

The biodistribution of isocyclosporin A and cyclosporin A in intraocular tissues was evaluated on sclera and uvea which were not separated during dissection. Therefore, the term "combined" in Table C above refers to the evaluation of biodistribution levels in sclera and uvea not separated during dissection.

The conversion of isocyclosporin A to cyclosporin A in ocular tissues over time was also measured and was minimal as expected both after single and repeated doses. The data obtained demonstrate that the direct effect of isocyclosporin A clearly accounts for the observed efficacy, thus evoking a novel and independent mechanism of action.

Example 2—Anti-Inflammatory Properties of Topically Applied Isocyclosporin a Eye Drops in a Rat Model of Ocular Alkali Burn The isocyclosporin A trifluoroacetate formulation of Example 1 was also tested in an acute rat model of ocular alkali burn. This was induced by application over the cornea for ten seconds of a filter paper disk soaked with 1N NaOH.

The experimental groups (n=6 each) consisted in a control group, that did not receive any eye drop treatment ("CTRL" group) and a group treated with the above described isocyclosporin ophthalmic solution ("New" group), by instilling ten microliters of the test formulation in each mouse three times for 24 hours.

The inflammatory infiltrate of the conjunctiva was then measured at the end of the treatment.

A significant reduction in the inflammatory infiltrate was observed in the treated group compared to untreated group, thus further confirming the active anti-inflammatory properties of topically applied isocyclosporin eye drops.

Furthermore, also in these animals, the conversion of isocyclosporin A to cyclosporin A was evaluated, as described above, and no significant interconversion was observed in both the ocular surface and/or intraocular tissues.

Example 3—Draize Eye Irritation Test

The typical Draize Eye Irritation test was carried out in the right eye of 6 healthy rabbits (3 per group) in order to compare tolerability of isocyclosporin A over cyclosporin A topical ophthalmic formulations (Draize, J. H., et al, *Journal of Pharmacology and Experimental Therapeutics* (1944), 82:377-390).

No behavioural reaction such as eye rubbing and no signs of ocular irritation (i.e. conjunctival reaction, swelling and/ or discharge) were observed in either group.

However, since an increased blink rate was observed in the cyclosporin A treated animals, the rabbit winking method described by Li et al (Li et al., Int. J Pharm, 2008;

363 (1-2): 177-182) was also carried out: ten seconds after the administration of the drop to the eyes, the frequency of the winking of the rabbits, for 2 minutes, was recorded.

The frequency was higher in the cyclosporin A group (9±1) as compared to the isocyclosporin A group (5±1), p<0.05.

Example 4—FLIPR Assay

The ability of isocyclosporin A and cyclosporin A to regulate the activation of ion channels involved in a number of inflammatory and/or allergic ocular diseases has been tested in a FLIPR assay.

The FLIPR assay is used to screen ion channel targets using membrane permeable fluorescent dyes. In particular, ion channel targets with significant Ca permeability, produce an increase in intracellular calcium that can be measured using calcium-sensitive dyes (Michelle R. Arkin et al. FLIPR™ Assays for GPCR and Ion Channel Targets. Assay Guidance Manual [Internet]. Bethesda (MD): Eli Lilly & Company and the National Center for Advancing Translational Sciences; 2004).

In details, the above described formulations containing isocyclosporin A or cyclosporin A at a concentration of 30 μM were tested in a FLIPR assay for their ability to activate or inhibit the ion channels TRPV3, TRPML2 or TRPC4. TRPV3 is an ionic channel that plays an important role in itching and inflammation, which are two characterizing aspects of ocular surface diseases such as VKC and AKC.

TRPML2 is an ionic channel with an important role in the context of the immune and inflammatory response.

TRPC4 is an ionic channel expressed by the corneal epithelium and which plays a role in the proliferation and migration of epithelial cells.

In details, human TRP cells are trypsinized, counted and seeded in black, clear-bottomed 96 well plates at a density of 50,000 cells per well and incubated overnight. Next day, media is removed from cell plates and 25 μl assay buffer is added. Red membrane potential or Calcium 5 dye solution (10 μl) is added to the wells and incubated at 37° C. for 1 hour. TRPV3, TRPML2 and TRPC4 are tested using the membrane potential dye.

Dye solution is made up in assay buffer. Compound dilutions are performed in 100% DMSO or dH2O then transferred to intermediate dilutions (5% DMSO/assay buffer or 5% dH2O/assay buffer) for a short time (<10 minutes) just before adding to the cell plate.

For agonist testing: The plates are placed in the FLIPR, after incubation with dye, and fluorescence monitored every 1.52 seconds. After 20 seconds IsoCsA, CsA or standard agonist are added to the wells and the fluorescence monitored for 5 minutes at ex./em. (excitation/emission wavelengths): 488 nm/510-570 nm.

For antagonist testing: isocyclosporin A or cyclosporin A was added, after incubation with dye, using manual multichannel and incubated for 10 minutes at room temperature. The plates are placed in the FLIPR and fluorescence monitored every 1.52 seconds. After 20 seconds 10 μl of the appropriate standard agonist is added and the fluorescence monitored for 5 minutes at ex/em: 488 nm/510-570 nm.

Reference agonists and antagonists have been tested against each channel to check that the value is within the acceptable range in order to validate the assays.

Percentage activation and inhibition values of the test compound and reference compounds has been evaluated.

No significant agonist activity has been detected whereas a marked inhibitory effect of isocyclosporin A as compared to cyclosporin A was observed. The results of the inhibition assay are reported in the following Tables 1-3.

Table 1 reports the percentage inhibition of TRPV3 by isocyclosporin A, cyclosporin A and reference compounds.

As can be seen from the data below, isocyclosporin A (IsoCsA in the table) has an ability to antagonize this channel more than 4 fold greater than cyclosporin A (CsA in the table).

TABLE 1 inhibition percentage of TRPV3
TRPV3

| Tested compound | Concentration | Inhibition % n = 1 | n = 2 | Mean | SD |
|---|---|---|---|---|---|
| Iso-CsA | 30 μM | 63.7 | 56.5 | 60.1 | 5.1 |
| CsA | 30 μM | 19.7 | 8.6 | 14.2 | 7.8 |
| Reference | 56 μM 2-APB | 0 | 0 | 0 | 0 |
| | 100 μM RR | 90.2 | 93.2 | 91.7 | 2.1 | in which 2-APB is 2-aminoetoxy diphenyl borate (agonist) and RR is ruthenium red (antagonist). As 2-APB is a reference standard agonist, i.e. causes activation of a receptor to produce a biological response, its inhibition % of TRPV3 is considered equal to 0%.

Table 2 reports the inhibition percentage of TRPML2 by isocyclosporin A, cyclosporin A and reference compounds.

As can be seen from the data below, isocyclosporin A (Iso-CsA in the table) has an ability to antagonize this channel more than double in comparison with cyclosporin A (CsA in the table).

TABLE 2 inhibition percentage of TRPML2
TRPML2

| Tested compound | Concentration | Inhibition % n = 1 | n = 2 | Mean | SD |
|---|---|---|---|---|---|
| Iso-CsA | 30 μM | 63.9 | 78.5 | 71.2 | 10.3 |
| CsA | 30 μM | 21.0 | 38.8 | 29.9 | 12.5 |
| Reference | 2 μM CaCl2 | 0 | 0 | 0 | 0 |
| | 4 mM Gd3 | 88.2 | 90.9 | 89.6 | 1.9 | in which CaCl2 is the agonist and Gadolinium Gd3 is the antagonist.

As CaCl2 acts as agonist, i.e. causes activation of a receptor to produce a biological response, its inhibition % of TRPML2 is considered equal to 0%.

TRPC4 is an ionic channel expressed by the corneal epithelium and which plays a role in the proliferation and migration of epithelial cells (Hua Yang et al, J Biol Chem. 2005 Sep. 16; 280 (37): 32230-7). Vernal keratoconjunctivitis (VKC) and atopic keratoconjunctivitis (AKC) are characterized by hyperproliferative phenomena of the ocular surface. Therefore, a molecule that can promote epithelial growth and migration in these pathologies could be detrimental.

Table 3 reports the activation percentage of TRPC4 by isocyclosporin A, cyclosporin A and reference compounds.

From the data below, it can be seen that while isocyclosporin A (Iso-CsA in the table) does not have any effect on activation of this channel, cyclosporin A (CsA in the table) acts as an agonist and therefore has undesired side effects due to its activation.

TABLE 3

| activation percentage of TRPC4 TRPC4 | | | | | |
|---|---|---|---|---|---|
| Tested | | Inhibition % | | | |
| compound | Concentration | n = 1 | n = 2 | Mean | SD |
| Iso-CsA | 30 μM | 2.5 | 0.8 | 1.7 | 1.2 |
| CsA | 30 μM | 33.5 | 32.9 | 33.2 | 0.4 |
| Reference | 200 nM Englerin A | 69.4 | 72.1 | 70.8 | 1.9 |
| | 25 mM GD3 | 0 | 0 | 0 | 0 | in which Englerin A is the agonist and Gadolinium GD3 is the antagonist.

As GD3 acts as antagonist, i.e. causes inhibition of a receptor to produce a biological response, its activation % of TRPC4 is considered equal to 0%.

The invention claimed is:

1. A method of treating an inflammatory and/or autoimmune ophthalmic disease in a human subject in need thereof, the method comprising the step of ophthalmically topically administering to the subject a composition comprising iso-cyclosporin A or an ophthalmically acceptable salt thereof.

2. The method of claim 1, wherein an inflammatory ophthalmic disease selected from a corneal and ocular surface inflammatory disease and an eyelid margin inflammatory disease is treated.

3. The method of claim 2, wherein the corneal and ocular surface inflammatory disease is selected from vernal kerato-conjunctivitis (VKC), atopic keratoconjunctivitis (AKC), allergic conjunctivitis, ocular rosacea, uveitis, dry eye disease (DED), ocular cicatricial pemphigoid (OCP), ocular graft-versus-host disease (GVHD), or immune corneal ulcers.

4. The method of claim 2, wherein the eyelid margin inflammatory disease is selected from inflamed pterygium or chronic blepharitis.

5. The method of claim 1, wherein the ophthalmically acceptable salt is selected from acetate, adipate, ascorbate, benzoate, benzenesulfonate, bicarbonate, bisulfate, butyrate, camphorate, camphorsulfonate, citrate, cyclohexyl sulfamate, ethanesulfonate, fumarate, glutamate, glycolate, hemisulfate, 2-hydroxyethylsulfonate, heptanoate, hexanoate, hydrochloride, hydrobromide, hydroiodide, hydroxymaleate, lactate, malate, maleate, methanesulfonate, 2-naph-thalenesulfonate, nitrate, oxalate, pamoate, persulfate, phenylacetate, phosphate, diphosphate, picrate, pivalate, propionate, quinate, salicylate, stearate, succinate, sulfamate, sulfanilate, sulfate, tartrate, p-toluenesulfonate, trifluoroacetate and undecanoate salts of isocyclosporin A.

6. The method of claim 1, wherein the composition is a liquid ophthalmic formulation.

7. The method of claim 6, wherein the liquid ophthalmic formulation is an eye drop liquid formulation.

8. The method of claim 7, wherein the liquid ophthalmic composition comprises an aqueous solution, a biphasic liquid formulation, a micro-emulsion, or a physiological saline solution.

9. The method of claim 1, wherein the composition a semi-solid ophthalmic formulation.

10. The method of claim 9, wherein the semi-solid ophthalmic formulation is a cream, an ointment, or a gel.

11. The method of claim 1, wherein the composition has a pH between 6 and 8.

12. The method of claim 1, further comprising administering at least one drug suitable for treatment of inflammatory and/or autoimmune ophthalmic diseases.

13. The method of claim 12, wherein the at least one drug comprises a corticosteroid.

14. The method of claim 1, further comprising administering a cyclosporin.

15. The method of claim 5, wherein the ophthalmically acceptable salt is a hydrochloride salt of isocyclosporin A.

16. The method of claim 5, wherein the ophthalmically acceptable salt is a trifluoroacetate salt of isocyclosporin A.

17. The method of claim 1, wherein the inflammatory and/or autoimmune ophthalmic disease is atopic keratocon-junctivitis (AKC).

18. A method of treating atopic keratoconjunctivitis (AKC) in a human subject in need thereof, the method comprising the step of ophthalmically topically administering to the subject a composition comprising isocyclosporin A or an ophthalmically acceptable salt thereof.

19. The method of claim 18, wherein the ophthalmically acceptable salt is a hydrochloride salt of isocyclosporin A.

20. The method of claim 18, wherein the ophthalmically acceptable salt is a trifluoroacetate salt of isocyclosporin A.

* * * * *